(12) United States Patent
Carpenter et al.

(10) Patent No.: US 10,294,267 B2
(45) Date of Patent: May 21, 2019

(54) MEMBRANE WITH SURFACE CHANNELS

(71) Applicant: Pall Corporation, Port Washinton, NY (US)

(72) Inventors: Gregory S. Carpenter, Mineola, NY (US); Munaf Tinwala, Roosevelt, NY (US); Stanley W. Kidd, Westbury, NY (US)

(73) Assignee: Pall Corporation, Port Washington, NY (US)

( * ) Notice: Subject to any disclaimer, the term of this patent is extended or adjusted under 35 U.S.C. 154(b) by 1334 days.

(21) Appl. No.: 14/096,289

(22) Filed: Dec. 4, 2013

(65) Prior Publication Data

US 2015/0152136 A1 Jun. 4, 2015

(51) Int. Cl.
| | |
|---|---|
| *C07K 1/34* | (2006.01) |
| *B01D 67/00* | (2006.01) |
| *B01D 69/10* | (2006.01) |
| *B01D 71/56* | (2006.01) |
| *B01D 71/06* | (2006.01) |
| *C07K 14/765* | (2006.01) |
| *C07K 16/00* | (2006.01) |
| *C08J 9/28* | (2006.01) |
| *B01D 69/02* | (2006.01) |
| *B01D 69/06* | (2006.01) |

(52) U.S. Cl.
CPC ............ *C07K 1/34* (2013.01); *B01D 67/0009* (2013.01); *B01D 67/0013* (2013.01); *B01D 69/02* (2013.01); *B01D 69/06* (2013.01); *B01D 69/10* (2013.01); *B01D 71/06* (2013.01); *B01D 71/56* (2013.01); *C07K 14/765* (2013.01); *C07K 16/00* (2013.01); *C08J 9/28* (2013.01); *B01D 2323/40* (2013.01); *B01D 2325/06* (2013.01)

(58) Field of Classification Search
None
See application file for complete search history.

(56) References Cited

U.S. PATENT DOCUMENTS

| | | | |
|---|---|---|---|
| 3,578,173 | A | 5/1971 | Streeton |
| 4,097,383 | A | 6/1978 | Ohtani et al. |
| 4,762,657 | A | 8/1988 | Rogers et al. |
| 6,277,282 | B1 | 8/2001 | Kihara et al. |
| 6,365,395 | B1 * | 4/2002 | Antoniou ............ B01D 61/142 210/767 |
| 7,208,200 | B2 | 4/2007 | Kools |

(Continued)

FOREIGN PATENT DOCUMENTS

| | | |
|---|---|---|
| CA | 2052605 A1 | 4/1993 |
| EP | 0 259 109 A3 | 8/1987 |

(Continued)

OTHER PUBLICATIONS

Madaeni, S. Journal of Porous Materials (2004) 11: 255. doi:10.1023/B:JOPO.0000046352.14487.6f.*

(Continued)

*Primary Examiner* — Heidi R Kelley
*Assistant Examiner* — Eric J McCullough
(74) *Attorney, Agent, or Firm* — Leydig Voit & Mayer

(57) ABSTRACT

Membranes having parallel channels in a surface of the membranes, wherein the channels have side walls having rough surfaces; filters and devices including at least one membrane, and methods of making and using the membranes, are disclosed.

20 Claims, 4 Drawing Sheets

(56) References Cited

U.S. PATENT DOCUMENTS

| | | |
|---|---|---|
| 7,959,780 B2 | 6/2011 | Hawkins et al. |
| 8,114,478 B1 | 2/2012 | Koreltz et al. |
| 8,309,265 B2 | 11/2012 | Miyauchi et al. |
| 2003/0121841 A1* | 7/2003 | Harttig ............... B01D 67/0009 210/321.84 |
| 2007/0072037 A1 | 3/2007 | Kamo et al. |
| 2010/0065490 A1 | 3/2010 | Balster et al. |
| 2010/0129720 A1 | 5/2010 | Sako et al. |
| 2011/0189575 A1 | 8/2011 | Moon et al. |

FOREIGN PATENT DOCUMENTS

| | | |
|---|---|---|
| EP | 0 259 109 A2 | 3/1988 |
| EP | 2366449 A2 | 9/2011 |
| JP | 578784 A | 1/1982 |
| JP | 61-136405 A | 6/1986 |
| JP | 63-69503 A | 3/1988 |
| JP | 11-165050 A | 6/1999 |
| JP | 2002066275 A | 3/2002 |
| JP | 2003-093853 A | 4/2003 |
| WO | WO 01/61042 A2 | 8/2001 |
| WO | WO 2009/137267 A2 | 11/2009 |
| WO | WO 2011/126363 A1 | 10/2011 |

OTHER PUBLICATIONS

Hobbs, C., S. Hong, J. Taylor. Effect of surface roughness on fouling of RO and NF membranes during filtration of a high organic surficial groundwater, Aqua 55(7), Oct. 2006.*

Singapore Search Report, Application No. 10201405252X, dated Dec. 15, 2014.

European Search Report Application No. 14 182 143.9, dated Jun. 1, 2015.

Bikel et al., *ICOM 2008*, "Phase Separation Microfabrication" Abstract, Jul. 2008.

Bikel et al., *Journal of Membrane Science*, "Shrinkage effects during polymer phase separation on microfabricated molds", 347 (2010), pp. 141-149.

* cited by examiner

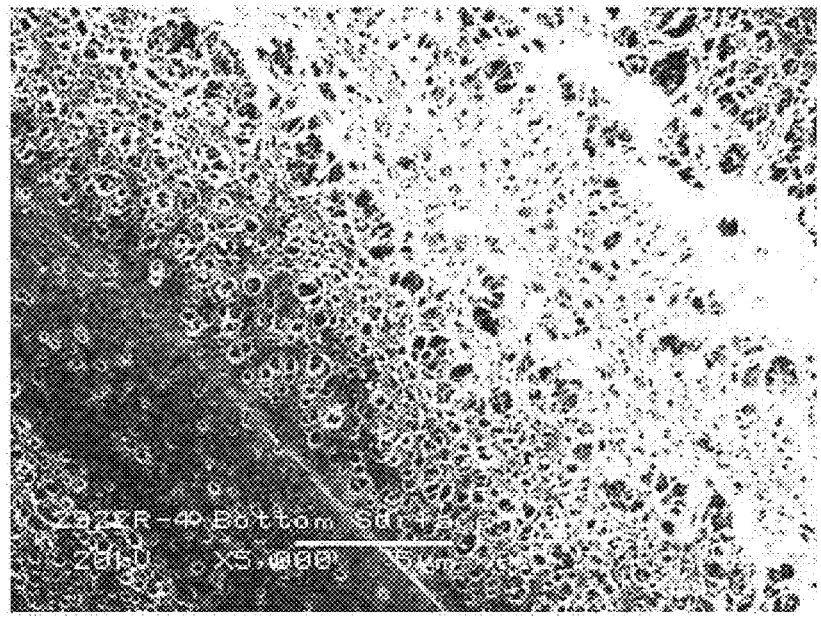
Figure 2
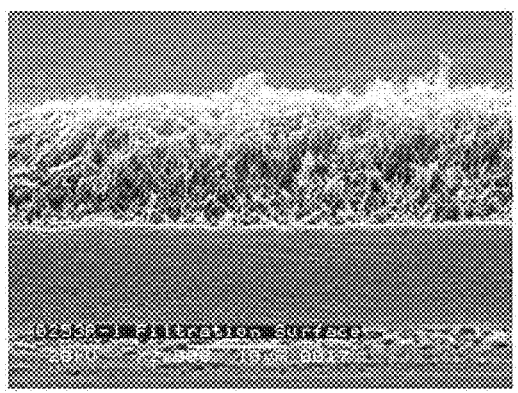 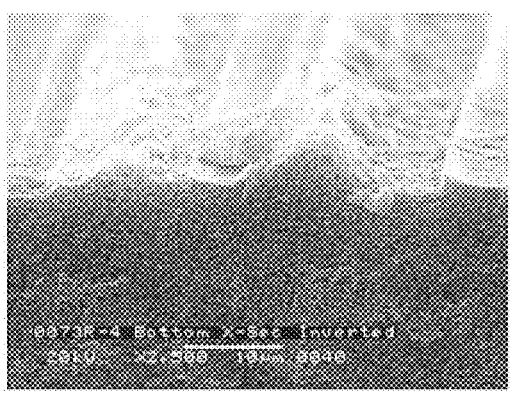
Figure 3A  Figure 3B

MEMBRANE WITH SURFACE CHANNELS

BACKGROUND OF THE INVENTION

Membranes can be used to filter a variety of fluids. For example, membranes are used to filter protein-containing fluids to remove undesirable material from the fluids and/or membranes are used to remove viruses from fluids. However, there is a need for improved membranes having higher protein capacity and/or virus removal capability.

The present invention provides for ameliorating at least some of the disadvantages of the prior art. These and other advantages of the present invention will be apparent from the description as set forth below.

BRIEF SUMMARY OF THE INVENTION

An embodiment of the invention provides a microporous membrane comprising a first surface and a second surface, wherein the first surface comprises lengthwise parallel surface channels, and wherein the channels have side walls comprising rough surfaces, the rough surfaces having an Ra in the range of from about 4.5 μin to about 19.0 μin. Typically, the side walls of the channels have rougher surfaces than the bottom walls of the channels. Typically, at least about 25% of the first surface has a plurality of parallel channels in the machine direction.

In another embodiment, a filter is provided, the filter comprising at least one membrane, preferably, at least two membranes.

A method of filtering fluid is also provided in accordance with another embodiment of the invention, the method comprising passing the fluid through the membrane or filter.

In another embodiment, a method of preparing a membrane is provided, the method comprising obtaining a substrate comprising a surface having a machine direction and a cross machine direction and having parallel abrasions in the surface in the machine direction; casting a polymer containing solution on the surface; exposing the solution to a phase inversion solution and forming a microporous membrane; and, removing the membrane from the substrate, wherein portions of the membrane contacting the parallel abrasions in the surface of the substrate are pulled away from the membrane, forming a membrane having a surface with parallel channels in the surface in the machine direction, the parallel channels having rough surfaces.

BRIEF DESCRIPTION OF THE SEVERAL VIEWS OF THE DRAWING(S)

FIG. 1A is a Scanning Electron Micrograph (SEM) showing the substrate-contacting surface of a membrane prepared in Example 3 after removing the membrane from a polyethylene terephthalate (PET) substrate with an untreated non-abraded surface. FIG. 1B is an SEM showing the substrate-contacting surface of a membrane prepared in Example 3 after removing the membrane from a polyimide substrate that was corona treated to provide a Critical Wetting Surface Tension (CWST) of 44 dynes/cm, wherein the substrate surface is non-abraded.

FIG. 2 is an SEM showing the substrate-contacting surface of a membrane prepared in Example 3 according to an embodiment of the invention after removing the membrane from a substrate with an abraded surface (wherein the surface is otherwise untreated).

FIG. 3 (A-B) are SEMs of the surface of the membrane prepared in Example 3 according to an embodiment of the invention, showing channels having side walls with rough surfaces. FIG. 3A is an SEM taken in the cross-machine direction, and FIG. 3B is an SEM taken in the cross-sectional direction.

DETAILED DESCRIPTION OF THE INVENTION

Figure 1A:

In accordance with an embodiment of the present invention, a microporous polymeric membrane is provided comprising (a) a first surface, comprising a microporous surface, (b) a second surface comprising a microporous surface; and (c) a microporous bulk between the first surface and the second surface; wherein the membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 to about 19.0 μin. In some embodiments, the side walls have rougher surfaces than the bottom walls.

In an embodiment, the side walls have rough surfaces having an Ra in the range of about 5 μin to about 9 μin. In another embodiment, the side walls have rough surfaces having an Ra in the range of about 9.5 μin to about 16.0 μin.

In an embodiment, at least about 25% of the first surface has the plurality of parallel channels in the machine direction, preferably, at least about 30% of the first surface has the plurality of parallel channels in the machine direction, and in some embodiments, at least about 35% of the first surface has the plurality of parallel channels in the machine direction. For example, in an embodiment, the membrane has in the range of from about 30% to about 45% of the first surface having the plurality of parallel channels in the machine direction.

Advantageously, membranes for removing viruses can be produced having less thickness than commercially available virus removal membranes while providing comparable or better virus removal efficiencies. As a result, membranes can be produced more cost effectively. The membrane can be a non-composite membrane, but can be sufficiently robust to the membrane to be pleated.

Alternatively, or additionally, membranes can be produced having an increased capacity to filter protein compared to conventional membranes without channels.

Filters comprising at least one inventive membrane, preferably, at least two inventive membranes, and well as filter devices comprising a housing and at least one inventive membrane, or a filter comprising at least one inventive membrane, are also provided according to embodiments of the invention.

A method of filtering fluid is also provided in accordance with another embodiment of the invention, the method comprising passing the fluid through at least one membrane, or a filter comprising at least one membrane, as described above. In one embodiment, a method comprises for removing undesirable material from a fluid comprises passing the fluid from a first surface of a microporous membrane through a second surface of the membrane, the first surface comprising a microporous surface, the second surface comprising a microporous surface; the membrane having a microporous bulk between the first surface and the second surface; wherein the membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 µin to about 19.0 µin. In a preferred embodiment of the method, the method comprises removing viruses from a protein containing fluid. In some embodiments of the method, fluid is passed through at least two membranes.

For example, in one embodiment, the method comprises passing the fluid from a first surface of a first microporous membrane through a second surface of the first membrane, the first surface comprising a microporous surface, the second surface comprising a microporous surface; the first membrane having a microporous bulk between the first surface and the second surface; wherein the first membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 µin to about 19.0 µin, and passing the fluid from the second surface of the first microporous membrane through a first surface of a second microporous membrane and through a second surface of the second membrane, the first surface of the second membrane comprising a microporous surface, the second surface comprising a microporous surface; the second membrane having a microporous bulk between the first surface and the second surface; wherein the second membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 µin to about 19.0 µin.

In another embodiment of the method for filtering fluid, the method comprises passing the fluid from a first surface of a first microporous membrane through a second surface of the first membrane, the first surface comprising a microporous surface, the second surface comprising a microporous surface; the first membrane having a microporous bulk between the first surface and the second surface; wherein the first membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 µin to about 19.0 µin, and passing the fluid from the second surface of the first microporous membrane through a second surface of a second microporous membrane and through a first surface of the second membrane, the second surface comprising a microporous surface, the first surface comprising a microporous surface, the second membrane having a microporous bulk between the second surface and the first surface; wherein the second membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 µin to about 19.0 µin.

In yet another embodiment of the method for filtering fluid, the method comprises passing the fluid from a second surface of a first microporous membrane and through a first surface of the first membrane, the second surface comprising a microporous surface, the first surface comprising a microporous surface, the first membrane having a microporous bulk between the second surface and the first surface; wherein the first membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 µin to about 19.0 µin, and passing the fluid from the second surface of the first microporous membrane through a second surface of a second microporous membrane and through a first surface of the second membrane, the second surface comprising a microporous surface, the first surface comprising a microporous surface, the second membrane having a microporous bulk between the second surface and the first surface; wherein the second membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 µin to about 19.0 µin.

In yet another embodiment of the method for filtering fluid, the method comprises passing the fluid from a second surface of a first microporous membrane and through a first surface of the first membrane, the second surface comprising a microporous surface, the first surface comprising a microporous surface, the first membrane having a microporous bulk between the second surface and the first surface; wherein the first membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 µin to about 19.0 µin, and passing the fluid from the second surface of the first microporous membrane through a first surface of a second microporous membrane and through a second surface of the second membrane, the first surface of the second membrane comprising a microporous surface, the second surface comprising a microporous surface; the second membrane having a microporous bulk between the first surface and the second surface; wherein the second membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 µin to about 19.0 µin.

In accordance with an embodiment of the invention, a method of preparing a membrane comprises obtaining a substrate comprising a surface having a machine direction and a cross machine direction and having parallel abrasions in the surface in the machine direction; casting a polymeric solution on the surface; effecting phase separation of the solution and forming a microporous membrane; and, peeling the membrane from the substrate, wherein portions of the membrane contacting the parallel abrasions in the surface of the substrate are pulled away from the membrane, forming a membrane having a surface with channels in the surface.

Without being limited to any mechanism, it is believed that, while producing the membrane, the phase inversion bath is not able to interact with (or interaction is reduced with) the surface of the membrane that it is attached to the substrate. Thus, skinning (that can reduce availability of pore channels) is reduced. Additionally, or alternatively, and again without being limited to any mechanism, it is believed that the substrate is physically entangled with the membrane, and when removing the membrane from the substrate after casting and precipitating the polymer, the physically entangled substrate (e.g., polyethylene terephthalate) pulls at the membrane, uncovering and providing surface pore channels that are available for filtration. Furthermore, and again without being limited to any mechanism, it is believed that the use of a substrate with machine direction abrasions or grooves allows for expulsion of air when the casting solution is applied to the substrate, thus reducing defects such as pinholes in the resultant membrane.

A variety of substrates are suitable for preparing membranes according to embodiments of the invention, as long as the substrate has parallel abrasions or grooves in the machine direction (along the length of the substrate). Preferably, the substrate is a non-paper substrate. Suitable substrates include, for example, a polyester such as polyethylene terephthalate (PET) (e.g., commercially available as MYLAR); polypropylene; polyethylene (including polyethylene naphthalate (PEN); polyethylene terephthalate glycol (PETG)); polyimide; polyphenylene oxide; nylon; and acrylics.

The abrasions/grooves in the substrates can be provided by a variety of processes, including scoring, e.g., by laser or mechanical abrasion. Preferably, the abrasions/grooves are prepared by scoring the surface of the substrate using an abrasive, such as an abrasive used for etching.

Typically, the substrate has in the range of about 15 to about 50 grooves/abrasions per mm in the cross-machine (width) direction, preferably, about 25 to about 35 grooves/abrasions per mm in the cross-machine (width) direction.

Typically, the Rz value (average depth between the highest peak and lowest valley in each sampling length) for the depth of the grooves in the substrate is in the range of from about 50 μin to about 175 μin, and the spacing between grooves is typically in the range of from 300 μin to about 2400 μin.

Optionally, and less preferably, the abraded/scored substrate can be further treated, e.g., corona-, e-beam-, or plasma-treated, before casting the polymer solution on the substrate.

Preferably, the membrane is prepared by an immersion phase inversion quench process. Typically, the phase inversion process involves casting or extruding polymer solution(s) into thin films on the abraded/grooved substrate, and precipitating the polymers through one or more of the following: (a) evaporation of the solvent and nonsolvent, (b) exposure to a non-solvent vapor, such as water vapor, which absorbs on the exposed surface, (c) quenching in a non-solvent liquid (e.g., a phase immersion bath containing water, and/or another non-solvent or solvent), and (d) thermally quenching a hot film so that the solubility of the polymer is suddenly greatly reduced. Phase inversion can be induced by the wet process (immersion precipitation), vapor induced phase separation (VIPS), thermally induced phase separation (TIPS), quenching, dry-wet casting, and solvent evaporation (dry casting). Dry phase inversion differs from the wet or dry-wet procedure by the absence of immersion coagulation. In these techniques, an initially homogeneous polymer solution becomes thermodynamically unstable due to different external effects, and induces phase separation into a polymer lean phase and a polymer rich phase. The polymer rich phase forms the matrix of the membrane, and the polymer lean phase, having increased levels of solvents and non-solvents, forms the pores.

The membrane is separated (e.g., peeled) from the substrate by a variety of suitable techniques as is known in the art.

A variety of polymer solutions are suitable for use in the invention, and are known in the art. Suitable polymer solutions can include, polymers such as, for example, polyaromatics; sulfones (e.g., polysulfones, including aromatic polysulfones such as, for example, polyethersulfone, polyether ether sulfone, bisphenol A polysulfone, polyarylsulfone, and polyphenylsulfone), polyamides, polyimides, polyvinylidene halides (including polyvinylidene fluoride (PVDF)), polyolefins, such as polypropylene and polymethylpentene, polyesters, polystyrenes, polycarbonates, polyacrylonitriles (including polyalkylacrylonitriles), cellulosic polymers (such as cellulose acetates and cellulose nitrates), fluoropolymers, and polyetherether ketone (PEEK). Polymer solutions can include a mixture of polymers, e.g., a hydrophobic polymer (e.g., a sulfone polymer) and a hydrophilic polymer (e.g., polyvinylpyrrolidone).

In addition to one or more polymers, typical polymer solutions comprise at least one solvent, and may further comprise at least one non-solvent. Suitable solvents include, for example, dimethyl formamide (DMF); N,N-dimethylacetamide (DMAc); N-methyl pyrrolidone (NMP); dimethyl sulfoxide (DMSO), methyl sulfoxide, tetramethylurea; dioxane; diethyl succinate; chloroform; and tetrachloroethane; and mixtures thereof. Suitable nonsolvents include, for example, water; various polyethylene glycols (PEGs; e.g., PEG-200, PEG-300, PEG-400, PEG-1000); various polypropylene glycols; various alcohols, e.g., methanol, ethanol, isopropyl alcohol (IPA), amyl alcohols, hexanols, heptanols, and octanols; alkanes, such as hexane, propane, nitropropane, heptanes, and octane; and ketone, ethers and esters such as acetone, butyl ether, ethyl acetate, and amyl acetate; acids, such as acetic acid, citric acid, and lactic acid; and various salts, such as calcium chloride, magnesium chloride, and lithium chloride; and mixtures thereof.

If desired, a solution comprising a polymer can further comprise, for example, one or more polymerization initiators (e.g., any one or more of peroxides, ammonium persulfate, aliphatic azo compounds (e.g., 2,2'-azobis(2-amidinopropane)dihydrochloride (V50)), and combinations thereof), and/or minor ingredients such as surfactants and/or release agents.

Suitable components of solutions are known in the art. Illustrative solutions comprising polymers, and illustrative solvents and nonsolvents include those disclosed in, for example, U.S. Pat. Nos. 4,340,579; 4,629,563; 4,900,449; 4,964,990, 5,444,097; 5,846,422; 5,906,742; 5,928,774; 6,045,899; 6,146,747; and 7,208,200.

While a variety of polymeric membranes can be produced in accordance with the invention, in preferred embodiments, the membranes are sulfone membranes (more preferably, polyethersulfone membranes and/or polyarylsulfone membranes), or semi-crystalline membranes (for example, PVDF membranes and/or polyamide membranes).

The membranes can be cast manually (e.g., poured, cast, or spread by hand onto the substrate) or automatically (e.g., poured or otherwise cast onto a moving bed having the substrate thereon).

A variety of casting techniques are known in the art and are suitable. A variety of devices known in the art can be used for casting. Suitable devices include, for example, roll coaters (forward or reverse roll coaters) or mechanical spreaders, that comprise spreading knives, doctor blades, or spray/pressurized systems. One example of a roll coater is a reverse roll coater, comprising a resin well into which the casting formulation (polymer containing solution) is introduced. A moving doctor roller and the coating gap regulate the distribution of the casting formulation onto the substrate. Illustratively, polymer containing solutions can be cast using a reverse roll coater having a gap between the doctor roller and the substrate in the range of, for example, about 5 to about 8 mils.

A variety of casting speeds are suitable as is known in the art. Typically, the casting speed is at least about 3 feet per minute (fpm), more typically in the range of from about 3 to about 40 fpm, in some embodiments, at least about 5 fpm.

The membranes can have any suitable pore structure, e.g., a pore size (for example, as evidenced by bubble point, or by $K_L$, as described in, for example, U.S. Pat. No. 4,340,479, or evidenced by capillary condensation flow porometry), a mean flow pore (MFP) size (e.g., when characterized using a porometer, for example, a Porvair Porometer (Porvair plc, Norfolk, UK), or a porometer available under the trademark POROLUX (Porometer.com; Belgium)), a pore rating, a pore diameter (e.g., when characterized using the modified OSU F2 test as described in, for example, U.S. Pat. No. 4,925,572), or removal rating media. The pore structure used depends on the size of the particles to be utilized, the composition of the fluid to be treated, and the desired effluent level of the treated fluid.

The porous surfaces of the membranes can have any suitable mean pore size, e.g., as determined by, for example, calculating the average surface pore size from an SEM at 5,000× or 20,000× magnification. Typically, at least the first microporous skin surface has a pore diameter of in the range of about 100 nm to about 450 nm in the channel walls and in the range of about 50 nm to about 300 nm in the channel bottoms.

Typically, the thickness of membranes according to embodiments of the invention is in the range of about 1.5 mils to about 6.5 mils, preferably, in the range of from about 3 mils to about 4 mils.

The membrane can have any desired critical wetting surface tension (CWST, as defined in, for example, U.S. Pat. No. 4,925,572). The CWST can be selected as is known in the art, e.g., as additionally disclosed in, for example, U.S. Pat. Nos. 5,152,905, 5,443,743, 5,472,621, and 6,074,869. Typically, the membrane has a CWST of greater than about 70 dynes/cm (about $70\times10^{-5}$N/cm), more typically greater than about 73 dynes/cm (about $73\times10^{-5}$N/cm), and can have a CWST of about 78 dynes/cm (about $78\times10^{-5}$N/cm) or more. In some embodiments, the membrane has a CWST of about 82 dynes/cm (about $82\times10^{-5}$N/cm) or more.

The surface characteristics of the membrane can be modified (e.g., to affect the CWST, to include a surface charge, e.g., a positive or negative charge, and/or to alter the polarity or hydrophilicity of the surface) by wet or dry oxidation, by coating or depositing a polymer on the surface, or by a grafting reaction. Modifications include, e.g., irradiation, a polar or charged monomer, coating and/or curing the surface with a charged polymer, and carrying out chemical modification to attach functional groups on the surface. Grafting reactions may be activated by exposure to an energy source such as gas plasma, vapor plasma, corona discharge, heat, a Van der Graff generator, ultraviolet light, electron beam, or to various other forms of radiation, or by surface etching or deposition using a plasma treatment.

A variety of fluids can be filtered in accordance with embodiments of the invention. Membranes according to embodiments of the invention can be used in a variety of applications, including, for example, sterile filtration applications, filtering fluids for medical applications (including for home and/or for patient use, e.g., intravenous applications), filtering fluids for the electronics industry, filtering fluids for the food and beverage industry, clarification, and/or filtering cell culture fluids. Preferably, membranes according to embodiments of the invention can be used in filtering fluids for the pharmaceutical industry, and filtering antibody- and/or protein-containing fluids.

A variety of undesirable materials can be removed from a fluid in accordance with embodiments of the invention. In a preferred embodiment, the undesirable material is a contaminant such as a virus, phage, or bacteria. Illustrative viruses and phages that can be removed include, for example phix174, PP7, PR772, MMV, and PPV. With respect to, for example, PP7 and PR772, typically, the log removal for PP7 is about 6 or greater when the challenge solution is concentrated as $10^7$ pfu/mL, and the log removal for PR772 is about 6 or greater when the challenge solution is concentrated as $10^6$ pfu/mL.

In accordance with embodiments of the invention, the membrane can have a variety of configurations, including planar, pleated, and/or hollow cylindrical.

Membranes according to embodiments of the invention are typically disposed in a housing comprising at least one inlet and at least one outlet and defining at least one fluid flow path between the inlet and the outlet, wherein at least one inventive membrane or a filter including at least one inventive membrane is across the fluid flow path, to provide a filter device or filter module. In an embodiment, a filter device is provided comprising a housing comprising an inlet and a first outlet, and defining a first fluid flow path between the inlet and the first outlet; and at least one inventive membrane or a filter comprising at least one inventive membrane, the inventive membrane or filter comprising at least one inventive membrane being disposed in the housing across the first fluid flow path.

Preferably, for crossflow applications, at least one inventive membrane or filter comprising at least one inventive membrane is disposed in a housing comprising at least one inlet and at least two outlets and defining at least a first fluid flow path between the inlet and the first outlet, and a second fluid flow path between the inlet and the second outlet, wherein the inventive membrane or filter comprising at least one inventive membrane is across the first fluid flow path, to provide a filter device or filter module. In an illustrative embodiment, the filter device comprises a crossflow filter module, the housing comprising an inlet, a first outlet comprising a concentrate outlet, and a second outlet comprising a permeate outlet, and defining a first fluid flow path between the inlet and the first outlet, and a second fluid flow path between the inlet and the second outlet, wherein at least one inventive membrane or filter comprising at least one inventive membrane is disposed across the first fluid flow path.

The filter device or module may be sterilizable. Any housing of suitable shape and providing an inlet and one or more outlets may be employed.

The housing can be fabricated from any suitable rigid impervious material, including any impervious thermoplastic material, which is compatible with the fluid being processed. For example, the housing can be fabricated from a metal, such as stainless steel, or from a polymer, e.g., transparent or translucent polymer, such as an acrylic, polypropylene, polystyrene, or a polycarbonated resin.

The following examples further illustrate the invention but, of course, should not be construed as in any way limiting its scope.

Example 1

This example demonstrates the preparation of a membrane according to an embodiment of the invention.

A polyethylene terephthalate (PET) (Mylar A, DuPont Teijin) substrate, 3 mil in thickness, is unwound and passed along a series of rollers, including a 10.75 inch OD abrasive roller (the abrasive roller coated with regularly spaced particles, ANSI designated roughness of 320 grit), the abrasive roller rotating co-current about 16 feet per minute (fpm) faster than the substrate, the substrate being drawn past the abrasive roller at a speed in the range of about 20 fpm, and the abraded substrate is wound on a final roller.

The grooves in the substrate have a depth of about 100 μin to about 150 μin as determined using a Pocket Surf III 1209 ML piezoelectric roughness meter (Mahr Metrology). The grooves are about 800 μin wide separated by a distance of about 400 μin (as measured using an Olympus BH2-UMA light microscope).

A solution is prepared consisting of 21.0% polyethersulfone (PES) E6020, mw 46-55,000 (BASF), 15.5% polyethylene glycol 200 (PEG200) (Dow Chemical), 12.7% acetic acid (AA) (JT Baker), 42.8% N,N-Dimethylacetamide (DMAc) (DuPont Chemical), and 8.0% Poly(1-vinylpyrrolidone-co-vinyl acetate) (Pasdone 5630, ISP Technologies). The abraded substrate is fed through a reverse roll coater at a speed of 5 fpm (with a gap between the doctor roller and the substrate in the range of from 5 to 8 mil wherein the rotational speed of the doctor roller is in the range of from 5-15 rpm), wherein the substrate abrasions are perpendicular to the lacquer well of the reverse roll coater, and the solution enters the abrasions in the substrate in the machine direction, displacing air from the substrate during casting. The solution is quenched in a liquid phase (DMAc/DI water at a ratio of 45:55) 21° C. inversion bath at a residence time of 2.2 minutes. Solvent is washed from the membrane by passing the membrane through DI water over a residence time of 9 minutes.

The membrane is peeled from the substrate by machine direction peeling at a speed in the range of 10-25 fpm, wherein the angle for peeling is maintained between 90 and 180 degrees, and the peeled membrane is wound over a DI water wetted interleaf material (polyphenyl sulfide), unwound from the interleaf material, dried by passing it through an oven at a speed of 10 fpm, and interleaved/rewound and leached in alcohol.

Example 2

This example demonstrates the preparation of a membrane according to an another embodiment of the invention.

An abraded substrate is prepared as described in Example 1. A solution is prepared consisting of 21.0% PES E6020, mw 46-55,000 (BASF), 16.5% PEG200 (Dow Chemical), 13.6% acetic acid AA (JT Baker), 45.5% DMAc (DuPont Chemical), and 3.5% (Pasdone S630, ISP Technologies). The solution is cast, quenched, and the membrane is peeled from the substrate, interleaved, dried, and rewound.

Example 3

This example illustrates the scored surface of a membrane (the membrane surface contacting and removed from an abraded surface of a substrate) according to an embodiment of the invention compared to the substrate-contacting surfaces of membranes removed from substrates having non-abraded surfaces.

A solution is prepared as described in Example 2, and cast on a PET (Mylar A, DuPont Teijin) substrate, 3 mil in thickness, wherein the surface of the substrate has not been abraded. The membrane is peeled from the substrate, interleaved, dried, and rewound. An SEM of the substrate-contacting surface is shown in FIG. 1A.

A solution is prepared as described in Example 2, and cast on a polymide substrate DuPont Kapton HN 3 mil that is corona treated to provide a CWST of 44 dynes/cm, wherein the surface of the substrate has not been abraded. The membrane is peeled from the substrate, interleaved, dried, and rewound. An SEM of the substrate-contacting surface is shown in FIG. 1B.

A membrane is prepared and peeled from an abraded surface as described in Example 2. SEMs of the substrate-contacting surface, and of the channels (longitudinal and later views) are shown in FIGS. 2 and 3, respectively.

Figure 1B:
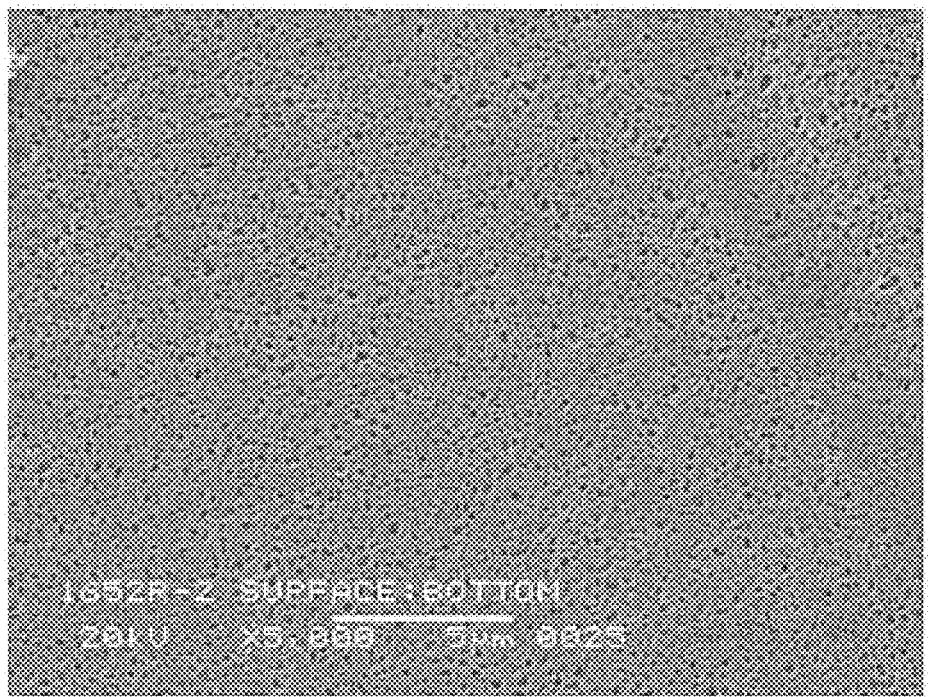

In contrast to FIGS. 1A and 1B, the surface of the embodiment of the membrane according to the invention shown in FIG. 2 shows more open pores, and the side walls of the channels have rough surfaces.

Example 4

This example describes the structure and dual layer (2 layers in sequence) filtration performance of the membranes prepared in Example 1.

The membranes are virus grade (nominal 20 nm) asymmetric membranes. The roughness of the walls of the channels (side walls and bottom walls) is determined using an atomic force microscope (AFM, Nanosurf Easyscan 2) and the "line roughness" tool from SPM control software (ver. 3.1). The line roughness tool allows for the selection of one-dimensional regions of the AFM and reports statistical measures for the variations in surface texture over the trace. Linear selections are taken in the grain (machine) direction of the channels in order to ensure that all points analyzed are selected at a constant elevation on the ridge. The raw texture data selected is corrected for gross linear deviations in height through the application of a "line fit" filter. The resulting roughness statistics are therefore independent of any linear trend in height variation over the selected surface.

The Ra values (the arithmetic average of the absolute values of the roughness profile ordinates, 1 Ra=1 microinch (μin)) of the side walls of the membranes are in the range of 5.4 to 8.9 μin, and the Ra values of the bottom walls are in the range of 0.5 to 1.7 μin.

Between about 30% to about 40% the surface areas of the first surfaces of the membranes have channels in the machine direction.

Membrane pore diameters for the retentive surface of the membranes (the non-channeled surface) are determined by SEM surface pore analysis, by calculating from an SEM at 20,000× magnification.

The retentive surface of the membrane has pore diameters in the range of about 20 nm to about 78 nm.

Membrane pore diameters for the channel walls (side and bottom) are determined by SEM surface pore analysis, by calculating from an SEM at 5,000× magnification.

Figure 4:
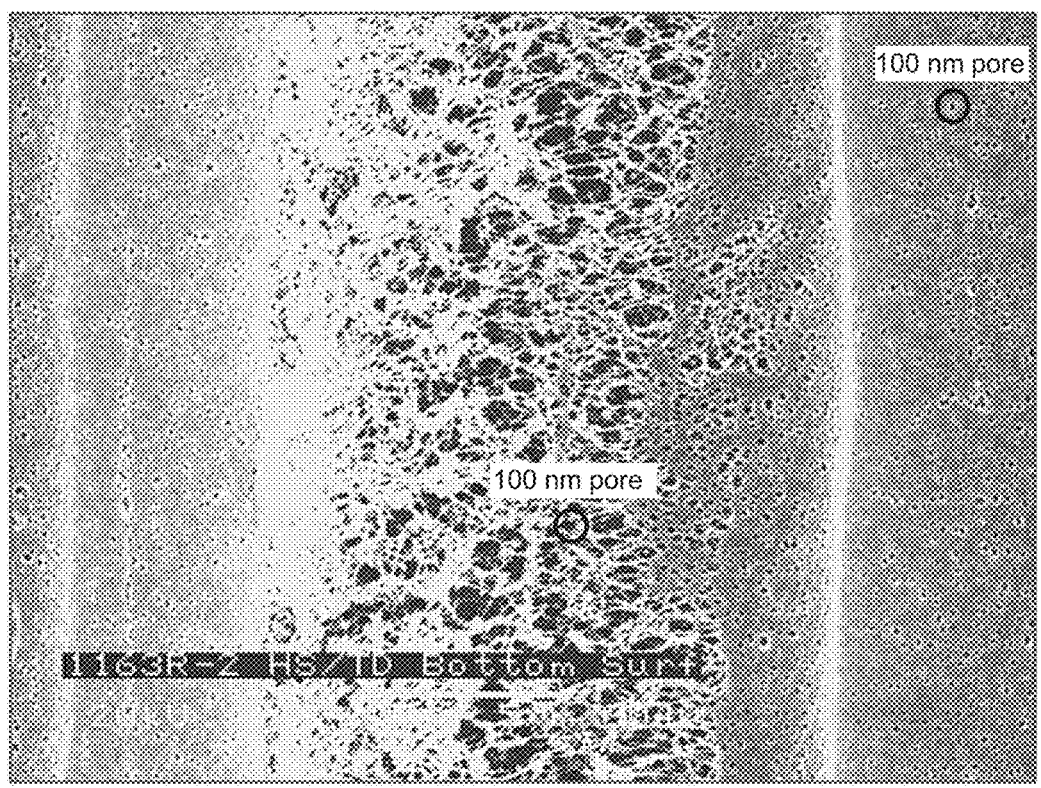
FIG. 4 is an SEM of the first surface of the membrane prepared in Example 1, with pore diameters identified in the channel side wall and the channel bottom wall.

The channel walls of the membranes have pore diameters in the range of about 100 nm to about 400 nm in the side walls, and in the range from about 50 nm to about 300 nm in the bottom walls. FIG. 4 shows an SEM of the first surface of this membrane, showing a 350 nm pore in the channel side wall, and a 100 nm pore in channel bottom wall.

Membrane pore diameters in the cross-sections described below with respect to the retentive surface are determined by SEM surface pore analysis, by calculating from an SEM at 10,000× magnification.

Measured from the downstream retentive surface, pores immediately above the surface have pore diameters in the range of from about 100 nm to about 400 nm, and pores in the bulk 2 µm above the surface have pore diameters in the range of from about 20 nm to about 80 nm. Pores in the bulk 4 µm above the surface have pore diameters in the range of from about 20 nm to about 120 nm. Pores in the bulk 6.5 µm above the surface have pore diameters in the range of from about 20 nm to about 280 nm.

Membrane pore diameters in the cross-sections described below with respect to the first surface (the scored surface or filtration surface) are determined by SEM pore analysis, by calculating from an SEM at 5,000× magnification.

Measured from the upstream filtration surface, pores immediately below the surface have pore diameters in the range of from about 100 nm to about 400 nm, typically about 280 nm.

Two membranes (each having a thickness of about 3 mils to about 4 mils) are stacked together to provide a filter, wherein the upstream surface of each membrane is a scored surface, i.e., the filter has an upstream scored surface of the first membrane followed by the downstream non-scored surface of the first membrane, and the scored surface of the second membrane contacts the downstream non-scored surface of the first membrane.

The membrane is challenged with 0.1 g/L SeraCare IgG (SeraCare Life Sciences, Milford, Mass.) in sodium acetate buffer. The IgG throughput (g/m$^2$) over 1 hour is 28.2.

The membrane is challenged with 1 wt % MP Biomedicals BSA solution (MP Biomedicals, Santa Ana, Calif.). The BSA throughput (kg/m$^2$) over 2 hours is 8.0.

The waterflow for the membrane is greater than 400 liters per square meter per hour (LMH).

Example 5

This example describes the structure and dual layer (2 layers in sequence) filtration performance of the membranes prepared in Example 2.

The membranes are virus grade (nominal 20 nm) asymmetric membranes. The roughness of the walls of the channels (side walls and bottom walls) is determined using an atomic force microscope (AFM, Nanosurf Easyscan 2) and the "line roughness" tool from SPM control software (ver. 3.1), as described in Example 4.

The Ra values of the side walls of the membranes are in the range of 9.5 to 15.6 µin, and the Ra values of the bottom walls are in the range of 0.5 to 1.7 µin.

Between about 30% to about 40% the surface areas of the first surfaces of the membranes have channels in the machine direction.

Membrane pore diameters for the retentive surface of the membranes (the non-channeled surface) are determined by SEM surface pore analysis, by calculating from an SEM micrograph at 20,000× magnification.

The retentive surface of the membrane has pore diameters in the range of about 20 nm to about 84 nm.

Membrane pore diameters for the channel walls (side and bottom) are determined by SEM surface pore analysis, by calculating from an SEM at 5,000× magnification.

Figure 5:
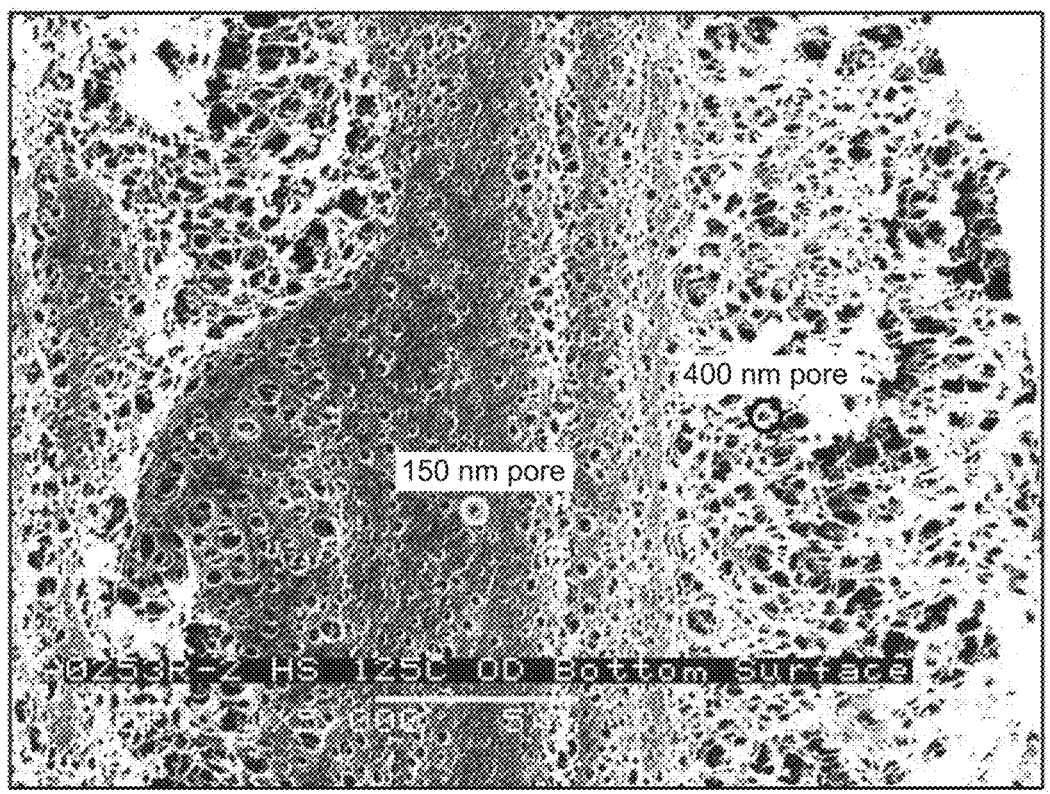
FIG. 5 is an SEM of the first surface of the membrane prepared in Example 2, with pore diameters identified in the channel side wall and the channel bottom wall.

The channel walls of the membrane have pore diameters in the range of about 100 nm to about 450 nm in the side walls, and in the range from about 50 nm to about 250 nm in the bottom walls. FIG. 5 shows an SEM of the first surface of this membrane, showing a 400 nm pore in the channel side wall, and a 150 nm pore in channel bottom wall.

Membrane pore diameters in the cross-sections described below with respect to the retentive surface are determined by SEM pore analysis, by calculating from an SEM at 10,000× magnification.

Measured from the downstream retentive surface, pores immediately above the surface have pore diameters in the range of about 100 nm to about 450 nm, and pores in the bulk 2 µm above the surface have pore diameters in the range of from about 20 nm to about 110 nm. Pores in the bulk 4 µm above the surface have pore diameters in the range of from about 20 nm to about 280 nm. Pores in the bulk 6.5 µm above the surface have pore diameters in the range of from about 20 nm to about 400 nm.

Membrane pore diameters in the cross-sections described below with respect to the first surface (the scored surface or filtration surface) are determined by SEM pore analysis, by calculating from an SEM at 5,000× magnification.

Measured from the upstream filtration surface, pores immediately below the surface have pore diameters in the range of from about 100 nm to about 450 nm, typically about 400 nm.

Two membranes (each having a thickness of about 3 mils to about 4 mils) are stacked together to provide a filter, wherein the upstream surface of each membrane is a scored surface, i.e., the filter has an upstream scored surface of the first membrane followed by the downstream non-scored surface of the first membrane, and the scored surface of the second membrane contacts the downstream non-scored surface of the first membrane.

The membrane is challenged with 0.1 g/L SeraCare IgG (SeraCare Life Sciences, Milford, Mass.) in sodium acetate buffer. The IgG throughput (g/m$^2$) over 1 hour is 12.

The membrane prepared according to Example 2 is challenged with 1 wt % MP Biomedicals BSA solution (MP Biomedicals, Santa Ana, Calif.). The BSA throughput (kg/m$^2$) over 2 hours is 3.8.

The waterflow for the membrane is greater than 250 LMH.

Example 6

This example demonstrates the preparation and dual layer (2 layers in sequence) filtration performance of a membrane according to another embodiment of the invention.

An abraded substrate is prepared as described in Example 1. A solution is prepared consisting of 7.71% Kynar 761 (Arkema), 7.71% Kynar 761A (Arkema), 2.72% comb polymer (Georez 48, Geochem), 57.30% DMAc (DuPont) and 24.56% ethyl acetoacetate (EAA, Eastman). The solution is cast, quenched, and the polyvinylidene fluoride (PVDF) membrane is peeled from the substrate and dried as described in Example 2.

The solution is also cast on cast on a PET (Mylar A, DuPont Teijin) substrate, 3 mil in thickness, wherein the surface of the substrate has not been abraded. The solution is quenched and the membrane is peeled from the substrate and dried.

Two membranes are stacked together to provide a filter. With respect to a filter including scored membranes, the upstream surface of each membrane is a scored surface, i.e., the filter has an upstream scored surface of the first membrane followed by the downstream non-scored surface of the first membrane, and the scored surface of the second membrane contacts the downstream non-scored surface of the first membrane.

The PVDF membranes are challenged with 0.5 g/L SeraCare IgG (SeraCare Life Sciences, Milford, Mass.) in sodium acetate buffer.

After 1 hour the PVDF membrane peeled from an abraded substrate according to an embodiment of the invention shows a 117.5% increase (on average) in IgG filtration capacity compared to the PVDF membrane peeled from a non-abraded substrate.

Example 7

This example demonstrates the ability of dual layer membrane filters according to embodiments of the invention to filter BSA and IgG solutions, compared to commercially available dual layer membrane filters. Each layer in the commercially available membrane filter contains a 3 layer composite virus filtering membranes.

Membranes are prepared as described in Example 1. The single layer membranes have thicknesses of about 3 mils to about 4 mils. Two membranes are stacked together to provide a filter, wherein the upstream surface of each membrane is a scored surface, i.e., the filter has an upstream scored surface of the first membrane followed by the downstream non-scored surface of the first membrane, and the scored surface of the second membrane contacts the downstream non-scored surface of the first membrane.

Commercially available composite multi-layer virus filtering membranes are obtained. The composite membranes have thicknesses of about 5 mils to about 6 mils. Obtained membranes are 2 membranes stacked together.

In the following challenges, the challenge is carried out at a constant differential pressure of 30 psi, and the flow rate is monitored during the challenge and the challenge is terminated when flux has decayed to 10% of the initial flux. Aliquots of filtered fluid are collected and assayed for (depending on the challenge) their phage, BSA, and IgG content.

The filters are challenged with 1 wt % MP Biomedicals BSA solution (MP Biomedicals, Santa Ana, Calif.) containing $10^7$ pfu/ml PP7 phages (25 nm nominal diameter) and $10^6$ pfu/ml PR 772 phages (53 nm nominal diameter) in phosphate buffered saline (PBS).

Additionally, filters are challenged with 0.1 g/L SeraCare IgG (SeraCare Life Sciences, Milford, Mass.) in sodium acetate buffer.

Comparing BSA throughput in kg/m$^2$, after two hours, the filter according to the invention processes about 8.0 kg/m$^2$, in contrast with about 5.4 kg/m$^2$ for the commercially available filter. Thus, filters according to an embodiment of the invention show about a 48% greater capacity to filter BSA solutions compared to the commercially available filters, wherein the differences are statistically significant according to a 2 sample t-test.

Both the filters according to an embodiment of the invention and the commercially available filters provide a PR772 titer retention of >6 @ 90% flux decay.

Both the filters according to an embodiment of the invention and the commercially available filters provide a PP7 titer reduction of >7 @ 90% flux decay.

Comparing IgG throughput in g/m$^2$, after 1.5 hours, the filters having 2 membranes according to the invention show capacities equivalent to those of the filters having 2 commercially available membranes (the differences are not statistically significant according to a 2 sample t-test).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A microporous polymeric membrane comprising
    (a) a first surface, comprising a microporous surface,
    (b) a second surface comprising a microporous surface; and
    (c) a microporous bulk between the first surface and the second surface;
    wherein the membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 µin to about 19.0 µin.

2. The membrane of claim 1, wherein the channels have side walls having rougher surfaces than the bottom walls.

3. The membrane of claim 1, wherein the side walls have rough surfaces having an Ra in the range of about 5 µin to about 9 µin.

4. The membrane of claim 1, wherein the side walls have rough surfaces having an Ra in the range of about 9.5 μin to about 16.0 μin.

5. The membrane of claim 1, wherein at least about 35% of the first surface has the plurality of parallel channels in the machine direction.

6. The membrane of claim 1, comprising a sulfone membrane.

7. The membrane of claim 6, comprising a polyethersulfone membrane.

8. The membrane of claim 1, comprising a polyamide membrane, or a PVDF membrane.

9. A filter comprising at least one membrane according to claim 1.

10. A filter comprising at least two membranes according to claim 1.

11. A method of removing undesirable material from a fluid, the method comprising passing the fluid from a first surface of a microporous membrane through a second surface of the membrane, the first surface comprising a microporous surface, the second surface comprising a microporous surface; the membrane having a microporous bulk between the first surface and the second surface; wherein the membrane has a machine direction and a cross machine direction, and the first surface has a plurality of parallel channels in the machine direction, wherein the channels have side walls and bottom walls, the side walls comprising rough surfaces, the rough surfaces having an Ra in the range of from about 4.5 μin to about 19.0 μin.

12. The method of claim 11, comprising removing viruses from a protein containing fluid.

13. A method of removing undesirable material from a fluid, the method comprising passing the fluid through the filter of claim 9.

14. A method of removing undesirable material from a fluid, the method comprising passing the fluid through the filter of claim 10.

15. A method of preparing a membrane comprising:
obtaining a substrate comprising a surface having a machine direction and a cross machine direction and having parallel abrasions in the surface in the machine direction, the parallel abrasions having a depth having an Rz value in the range of from about 50 μin to about 175 μin;
casting a polymeric solution on the surface;
effecting phase separation of the solution and forming a microporous membrane; and,
peeling the membrane from the substrate, wherein portions of the membrane contacting the parallel abrasions in the surface of the substrate are pulled away from the membrane, forming a membrane having a surface with parallel channels in the machine direction, wherein the channels have side walls and bottom walls, the side walls comprising rough surfaces, the rough surfaces having an Ra in the range of from about 4.5 μin to about 19.0 μin.

16. The membrane of claim 3, comprising a sulfone membrane.

17. The membrane of claim 4, comprising a sulfone membrane.

18. The membrane of claim 3, comprising a polyamide membrane, or a PVDF membrane.

19. The membrane of claim 4, comprising a polyamide membrane, or a PVDF membrane.

20. A filter comprising at least two membranes according to claim 6.

* * * * *